United States Patent [19]

Seitz

[11] Patent Number: 5,387,184
[45] Date of Patent: Feb. 7, 1995

[54] ORTHOPAEDIC DEVICE OF THE NON-ISCHIAL WEIGHT BEARING KIND

[75] Inventor: Michael W. Seitz, Pretoria, South Africa

[73] Assignee: Technology Finance Corporation (Proprietary) Limited, Sandton, South Africa

[21] Appl. No.: 86,628

[22] Filed: Jul. 1, 1993

[30] Foreign Application Priority Data

Jul. 1, 1992 [ZA] South Africa ............... 92/4894

[51] Int. Cl.$^6$ ............................................. A61F 5/00
[52] U.S. Cl. ................................................ 602/23; 602/6
[58] Field of Search .................. 602/5, 6, 7, 12, 16, 602/23–26

[56] References Cited

U.S. PATENT DOCUMENTS

| | | | |
|---|---|---|---|
| 1,490,265 | 4/1924 | Glasgow | 602/23 |
| 2,516,253 | 7/1950 | Pieterick . | |
| 2,573,866 | 11/1951 | Murphy | 602/23 X |
| 2,827,897 | 3/1958 | Pawlowski . | |
| 4,494,534 | 1/1985 | Hutson | 602/23 X |
| 5,020,790 | 6/1991 | Beard et al. | 602/23 X |
| 5,121,747 | 6/1992 | Andrews | 602/23 X |

FOREIGN PATENT DOCUMENTS 2329251  5/1977  France .
90/7699  7/1991  South Africa .

OTHER PUBLICATIONS

Medizinisch–Orthopadische Technik, vol. 101, No. 2, 1981 pp. 39–41, Nitschke 'Laterale Hüft–Knie–Fuss–Orthesen'.

Primary Examiner—Richard J. Apley
Assistant Examiner—Linda C. M. Dvorak
Attorney, Agent, or Firm—Darby & Darby

[57] ABSTRACT

An orthopaedic caliper 40 has an orthopaedic device 42 having a lower portion 48 and an upper portion 50. The portion 48 is attached snugly and not tightly, to a thigh. The upper portion 50 is a moulding of deformable, stretch resistant material. It is of concave or cradle shape to fit an upper portion of the thigh and a lower portion of a buttock. The portion 48 cannot dig into soft tissue and thus cannot become ischial weight bearing. It merely exerts a predominantly horizontal force on the body. This causes the user to assume a substantially normal posture and gait and the leg bones of the user to bear the weight. A bulge 50.3, to accommodate the buttock, collapses when the user is seated to prevent pressure points on bony protuberances and pressure underneath the thigh.

4 Claims, 4 Drawing Sheets

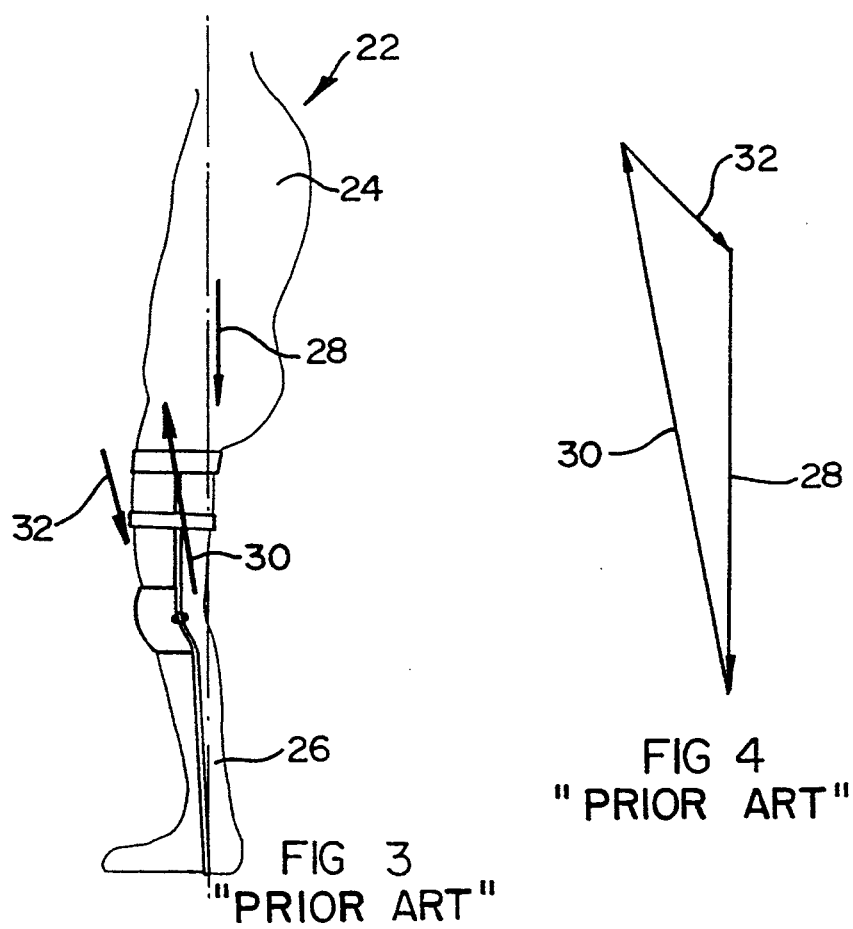
FIG 3 "PRIOR ART"
FIG 4 "PRIOR ART"
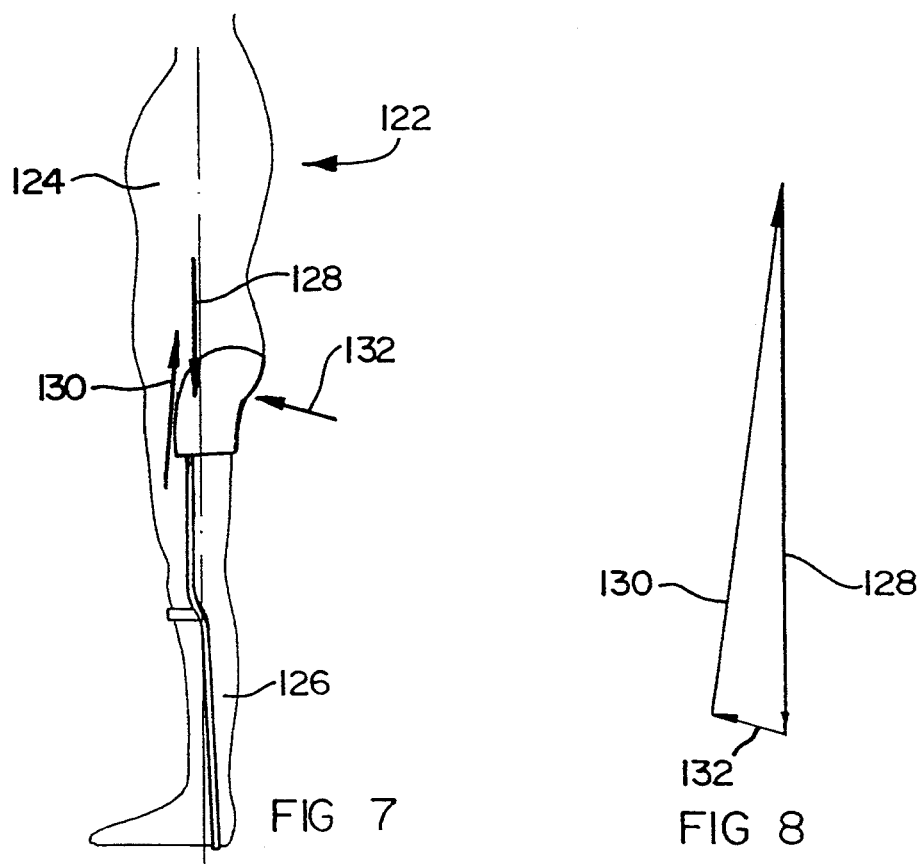
FIG 7
FIG 8

ORTHOPAEDIC DEVICE OF THE NON-ISCHIAL WEIGHT BEARING KIND

FIELD OF THE INVENTION

This invention relates to an orthopaedic device, more specifically to an orthopaedic device suitable to form part of an orthopaedic caliper. It relates further to an orthopaedic caliper and also to conversion of an orthopaedic caliper.

BACKGROUND OF THE INVENTION

The Applicant has identified a problem in conventional orthopaedic calipers which is symptomized by the "paraplegic gait" or posture taken up by paraplegics (and others) when standing with the aid of calipers. Such posture is typified by hyperextension (pushing forward) of the hips, backward pelvic tilt and the resultant lying backwards of the torso. The Applicant believes that the underlying reason for such a posture, is that a conventional caliper, even though it may purport to be non-ischial weight bearing, is nevertheless in practice at least partially weight bearing on the ischial tuberosity and/or on the soft thigh and buttock tissue of the user in that such tissue "seats" on the upper edge of the caliper. This problem is described herein below with reference to FIGS. 1 to 4 of the drawings.

It is thus an object of this invention to provide an orthopaedic caliper which is substantially non-ischial weight bearing and which is functionally more effective than a conventional caliper.

SUMMARY OF THE INVENTION

In accordance with the invention, there is provided an orthopaedic device, which is suitable to form part of an orthopaedic caliper and which comprises a lower portion which is stiff and to which depending components of said orthopaedic caliper will be located in use, the lower portion having an abutment surface positioned to abut the thigh of a user; and an upper portion which is attached to or attachable to the lower portion to extend upwardly from the lower portion in use and which is in the form of a moulding, the upper portion having a shape which is concave and which is generally complemental to an upper rear portion of the thigh and a lower portion of a buttock of the user when standing, the upper portion being of a material which is stretch resistant and which is deformable so as to conform to the shape of the upper portion of the thigh and lower buttock of the user when seated, the stretch resistance and the concave shape of the upper portion allowing the upper portion to exert a force having a horizontal component against the user when standing.

The lower portion may be in the form of a collar receivable around the thigh of a user. Instead, preferably, it may be part annular only including a tying element of soft material. It may be in the form of a moulding of polypropylene material or other similar material. Instead, it may be in the form of a band, e.g. of steel or other metal, but this is not preferred.

The upper section may be of synthetic plastics or other mouldable material. It may be of thin polypropylene material or other, similar, material having the required characteristics. It may be moulded into the lower portion. Instead, it may be attached to the lower portion, e.g. adhesively.

The invention extends to an orthopaedic caliper having, toward an upper end thereof, body attachment means in the form of a new orthopaedic device in accordance with this invention as herein described.

The invention extends further to a method of converting a conventional orthopaedic caliper into an orthopaedic caliper in accordance with this invention, the method including replacing conventional body attachment means of the conventional caliper with a new orthopaedic device in accordance with this invention and as herein described.

The invention accordingly extends to an orthopaedic caliper converted in accordance with this invention.

The invention is now described, in contrast to the prior art, with reference to the accompanying diagrammatic drawings.

BRIEF DESCRIPTION OF THE DRAWINGS

FIG. 3 shows, in side view, a user using the conventional caliper of FIG. 1, and forces which are operative in supporting the user with the aid of the conventional caliper;

FIG. 4 shows, schematically, a force diagram in accordance with the arrangement of FIG. 3;

FIGS. 7 and 8 correspond respectively to FIGS. 3 and 4, but in respect of the arrangement with the caliper of FIG. 5 in accordance with this invention.

DETAILED DESCRIPTION OF THE INVENTION

Figure 1:
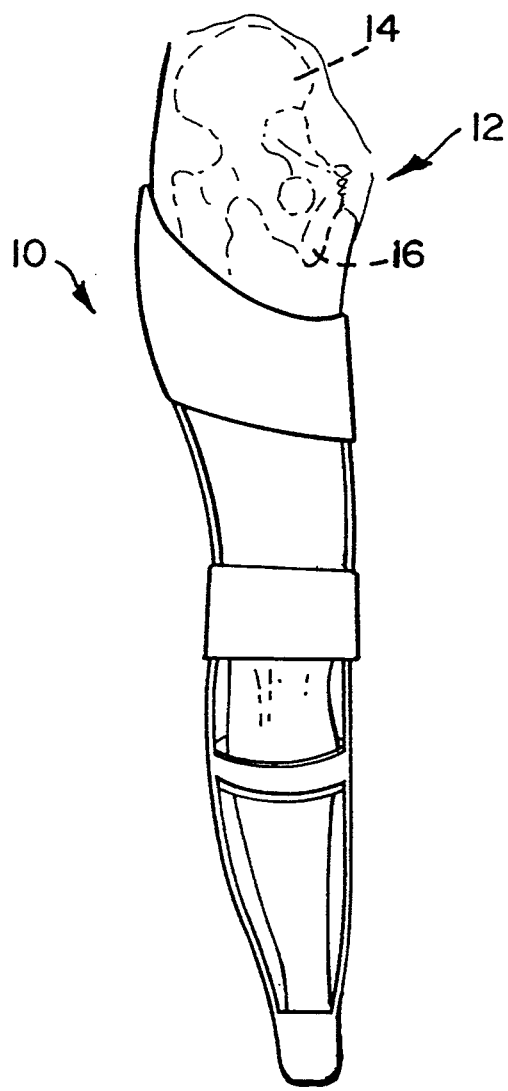
FIG. 1 shows, in rear view, a conventional (i.e. prior art) orthopaedic caliper or leg brace (intended to be non-ischial weight bearing) in use on a left leg of a user.

With reference to FIG. 1 of the drawings, a prior art orthopaedic caliper is shown, indicated by reference numeral 10. It is of the (supposedly) non-ischial weight bearing kind. It is shown in use in association with the left leg 12 of a user. A left hip bone 14 of the user is shown in dotted, including the ischial tuberosity 16 at the lower end of the hip bone 14.

This arrangement is illustrated in FIG. 3 in side view where it can be seen that, for the caliper 10 to operate, the person 22 using the caliper has to hyper-extend (push forward) his hips with resultant leaning back of the torso 24. Also the legs 26 of the person slant rearwardly and downwardly from the hips. Such hyperextension allows a rear top edge of the caliper to "dig in" and abut the ischial tuberosity/soft tissue of the user.

The forces in play to support the person 22 are generally shown by arrows in FIG. 3 and they are redrawn in the form of a force diagram in FIG. 4. The body weight 28 of the person 22 operates through the centre of gravity of the person i.e. through a point at a lower end of the torso above the hips, and works vertically downwardly. The main force operating to counteract the body weight 28 is partially exerted by the caliper 10 on the ischial tuberosity and/or soft tissue of the thigh and hip and is partially carried by the leg bones of the user.

Said main force is indicated by reference numeral 30. As the forces 28 and 30 do not operate in directly opposed directions and because the ischial tuberosity does not coincide with the centre of gravity, a third force, namely a tension force 32, is required to close the force diagram as shown in FIG. 3 and thus to result in a stable situation allowing the person 22 to stand. The stabilizing force 32 is accomplished by tension in ligaments, muscle and tissues along the front of the hips/thighs of the person 22.

The prior art caliper and the way it supports the human body have many disadvantages, symptomized by the posture of the user as shown in FIG. 3, which posture is also known as "paraplegic gait". Those disadvantages are merely briefly mentioned as they are well known in the field of the invention. The posture of the person is uncomfortable and leads to fatigue and other undesirable side effects like unnatural muscle position, excessive compensating dorsal kyphosis, undesirable stress on other parts of the anatomy like the lower back, an inefficient walking aid, poor leg extension requiring extensive strapping, and the like. To enable the person to use the caliper for support, it is necessary to tie the body attachment means tightly around the person's legs, thus squeezing or pressuring the soft tissue. Furthermore, the person's leg including the leg bones are to a large extent inactive whereas they would have benefited by being as active as possible. These features, and further complications, so the Applicant believes, can be shown in biomechanical analysis to have their primary origins in hyperextension of the hips or knee flexion, resulting in backward pelvic tilt.

The backward pelvic tilt that occurs when using a conventional caliper results from a small increase in knee flexion when the hip is hyperextended during standing. This knee flexion occurs since the relatively short lever arm of the caliper (above knee joint) exerts localized forces on the posterior aspect of the thigh, depressing the soft tissue. Tightening the caliper thigh straps to depress the soft tissue prior to standing reduces this knee flexion, but increases the circumferential pressure on the leg. This circumferential pressure is uncomfortable and physiologically undesirable. Furthermore, the caliper may become weight bearing if the caliper cuff/band is fixed too high (to increase the lever arm above the knee) and is forced by the thigh strap below the ischium.

Also the caliper, which now partially has to bear the weight of the person, is unduly stressed and wears out prematurely.

In another type of conventional calipers, the so-called ischial weight bearing type, attempts have been made to load the ischial tuberosity and to unload the leg bones. One such embodiment is illustrated in use in FIG. 2. It is not described and like reference numerals refer to like features. In such embodiment, it is tightly secured to the user's body such that an upper seat portion thereof provides a seat for the ischial tuberosity.

Figure 2:
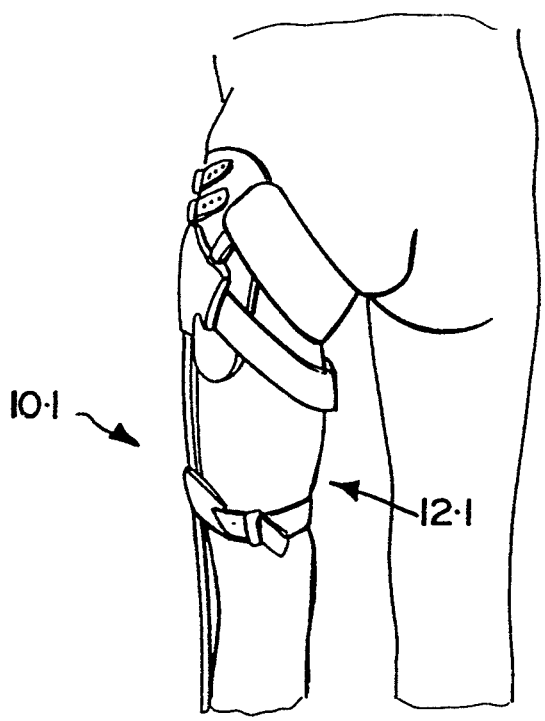
FIG. 2 shows, in a view corresponding to FIG. 1, another conventional (i.e. prior art) orthopaedic caliper or leg brace (intended to be ischial weight bearing)

The FIG. 2 caliper is intended for use when the leg bones cannot be loaded. It operates entirely differently to a caliper of this invention. A caliper of this invention is intended to load the leg bones, and is thus not intended to replace a caliper of the ischial weight bearing kind.

Figures 5, 6:
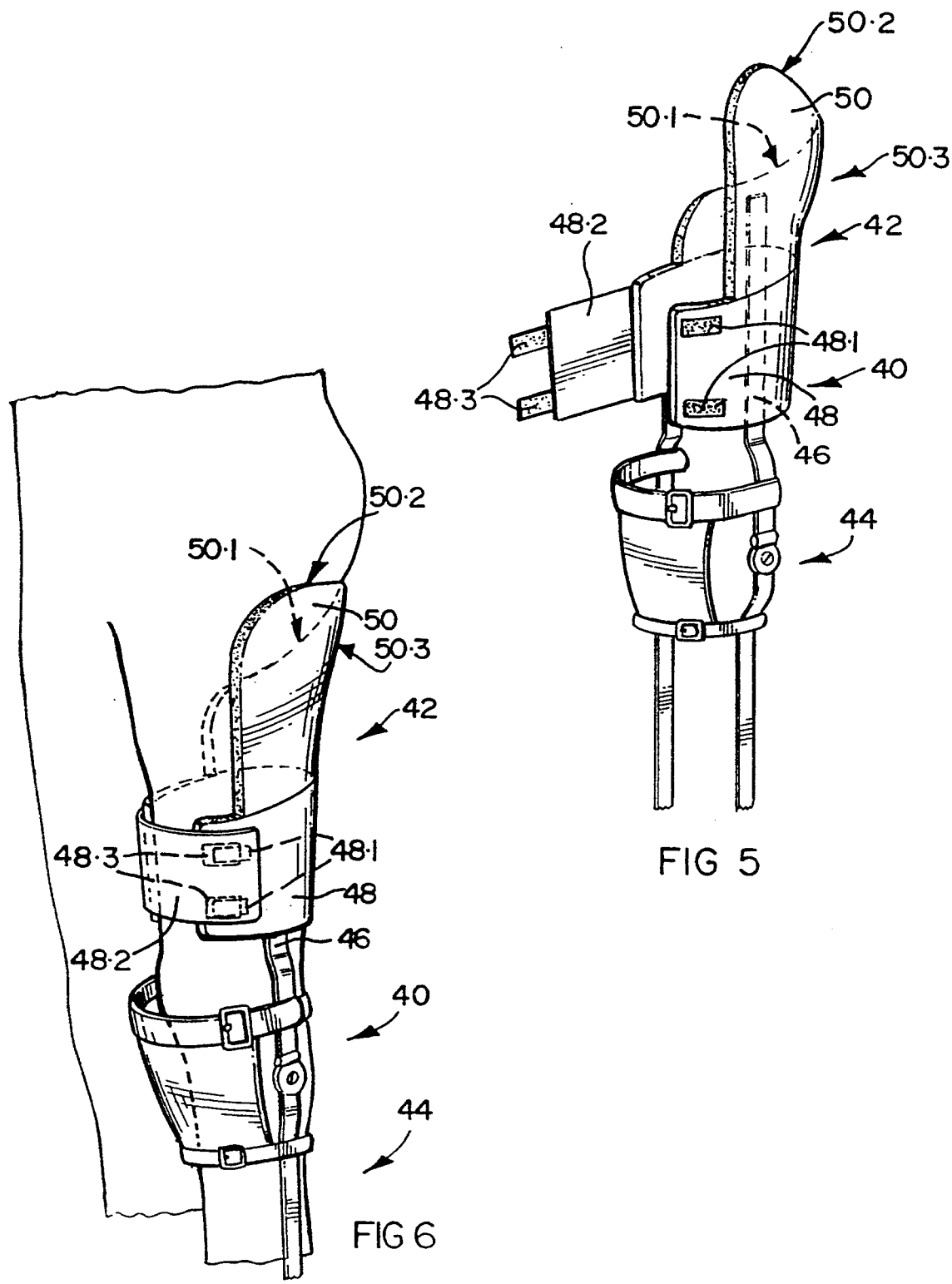
FIG. 5 shows, in three-dimensional view, an orthopaedic caliper in accordance with this invention.
FIG. 6 shows, in three-dimensional side view, the orthopaedic caliper of FIG. 5 is use.

With reference to FIGS. 5 and 6, a caliper in accordance with this invention is generally indicated by reference numeral 40. It comprises an orthopaedic device 42 toward an upper end thereof which orthopaedic device is in accordance with this invention. The caliper 40 further comprises a depending portion 44 which can be conventional. The orthopaedic device 42 is mounted on elongate supports 46 extending upwardly from the depending portion 44.

The orthopaedic device 42 has a lower portion in the form of a collar 48 which is receivable around the thigh of a user. For that purpose, it is conveniently discontinuous to allow easy access for the thigh and can then be tied to the person's thigh by means of a flap 48.2 and attachment means in the form of strips 48.1 having hooks and complementary strips 48.3 having eyes (available in the trade under the trademark VELCRO), respectively applied to the flap 48.2 an the collar 48, as shown in FIGS. 5 and 6. It is emphasised that the lower portion 48 is merely snugly located on the person's thigh, i.e. it is not tightly strapped to the thigh like in conventional calipers.

The orthopaedic device 42 further comprises an upper portion generally indicated by reference numeral 50. The upper portion 50 is in the form of a moulding of synthetic plastics material like thin polypropylene and is generally concave in the form of a composite cradle cradling the rear upper portion of the person's thigh and a portion of his buttock. The upper portion may conveniently be moulded into the lower portion 48. Instead, it may be located within the lower portion e.g. adhesively.

The upper portion 50 is moulded to have a low profile, as indicated by reference numeral 50.1, along its medial side in use. It has a relatively high profile, as indicated by reference numeral 50.2, along its outer side in use, but this is not a requirement. Along the rear, it may be moulded to have a slight bulge, as indicated by reference numeral 50.3, to follow the buttock contour of the user.

It is to be appreciated that the material of the upper portion is soft or pliable but is nevertheless stretch resistant. However, in the concave or cradle-like form it assumes and when stabilized against the lower portion 48, it is stiff enough to be resistant against bending and it can exert a force on the thigh and buttock of the user which force has a predominantly horizontal forward component.

It is emphasised that the lower portion 48 is stabilised on the thigh of the user such that it can exert horizontal force components (i.e. generally perpendicular to adjacent body surfaces of the user) and that it is not tight to the extent that it can exert large vertical force components (i.e. generally along adjacent body surfaces of the user). Thus, it does not squeeze or pressurise the soft tissue of the thigh unduly. Furthermore, the upper portion 50, as described above, can exert horizontally forward force components on the body of the user but does not promote flexion of the hips. It thus does not allow large vertical force components to be applied to the body. Thus, and with reference to FIG. 7, a user has a posture which is akin to that of a normal person and which is substantially different to the "paraplegic gait" illustrated in FIG. 3.

With reference to FIG. 8, the forces in play include a vertically downward force indicated by reference numeral 128 representing the body weight of the user and acting vertically downwardly through the person's centre of gravity. Furthermore, and this is very important in the context of the invention, the body weight of the person is largely balanced by a force in the leg bones of the person as indicated by reference numeral 130 which force acts through the hip joint of the person in a manner similar to that of a normal person. The forces 128 and 130 are illustrated in FIG. 8 and it can also be seen that only a relatively small stabilizing force, operating in a direction which is substantially horizontally forward, is required to close the force diagram. The stabilising force is indicated by reference numeral 132 and is in practice exerted by the upper portion 50 onto the rear of the thigh and the buttock of a user. It is important to appreciate, first, that the magnitude of the force 132 is small, and, second, that the direction of the force is such that its component perpendicular to the body surface of the user is predominant.

The mechanical action of the orthopaedic device 42 is to direct the posterior forces. which are conventionally exerted on the thigh (femur), to the buttock (back of the ischium). This position is mechanically superior as it increases the lever arm of the caliper reducing the magnitude of the proximal posterior forces. These forces are distributed on the buttock (i.e. primarily to the back of the ischium) and promote rotation of the pelvis and thus hip extension.

Figure 9:
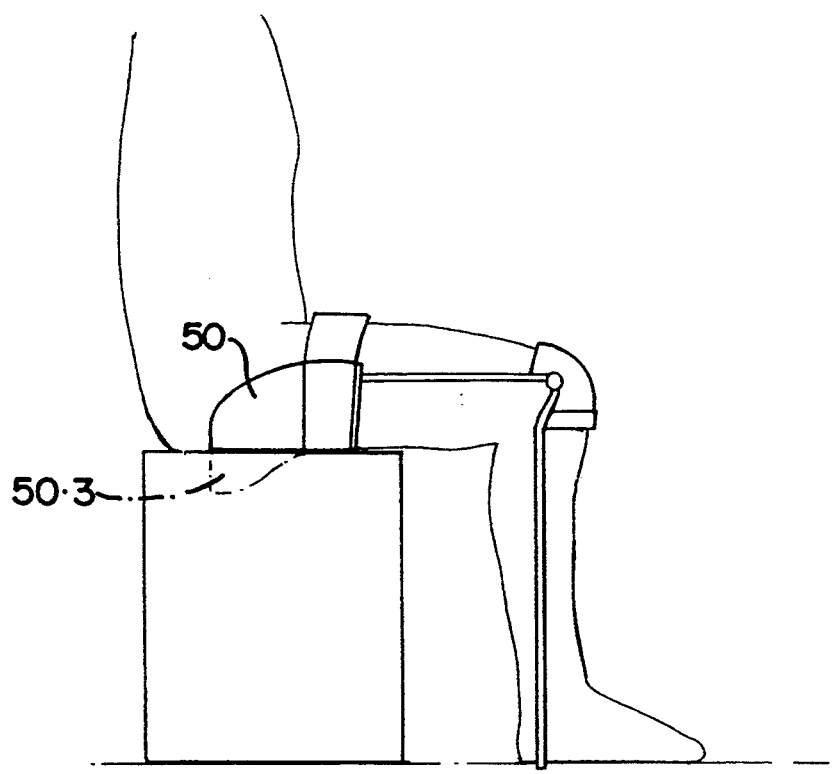
FIG. 9 shows, in side view a user of the caliper of FIG. 5 in accordance with this invention, in a seated condition.

With reference to FIG. 9, it is shown that the person 122 using the caliper 40 is in a seated condition with the rear of his thigh and the lower part of his buttock generally in a common plane dictated by the seat surface. Reference numeral 50.3, in ghost lines, shows the outline the bulge 50.3 would have taken up, i.e. when in its relaxed condition, but for the presence of the seat surface. The seat surface, however, deforms the upper portion 50 to conform with the seat surface. Such deformation is made possible, without undue discomfort to the user 122, by having the upper portion of relatively soft deformable material. It is emphasized that such deformation causes inward collapsing of the material. It does not cause excessive stretching or permanent deformation as the material is stretch resistant. In this regard, it is emphasized that comfort when seated is very important, because a user is normally seated for a major portion of the time a caliper is worn.

The invention has a large number of advantages, inter alia that the unnatural and undesirable "paraplegic gait" is to a large extent eliminated and the stresses on the body of a person are much more similar to those of a normal person. Furthermore, the leg bones of a user are used to a large extent to carry the person's weight thus activating at least the leg bones and the joint of the user, which is desirable. Furthermore, because the caliper is used primarily to stabilize the user's leg and not to carry the weight, it is stressed to a much lower degree. Thus, the caliper can be made lighter than in conventional calipers, which greatly adds to the comfort of the user. Furthermore, because the caliper is no longer weight bearing to a large extent, attachment to the body of the user is mostly for location and the forces exerted are small and are directed such that force components perpendicular to the body surfaces of the user are predominant, thus allowing snug fitting rather than tight fitting which, to a large extent, reduces or even eliminates pressuring and squeezing of soft tissue.

It is regarded as of considerable importance that the shape, construction and material of the upper portion of the orthopaedic device allow the bulging shape thereof to fold or collapse when a user is seated, thus preventing pressure points on bony prominances (the ischial tuberosity) and preventing undue pressure underneath the thigh.

It is further regarded as an important advantage that the upper portion, naturally, within limits, takes on the shape and size of the relevant portions of a user's body. Thus, it is believed that it will not be necessary to custom make an orthopaedic device in accordance with the invention, for a majority of users. It is believed that a limited number of sizes, e.g. large, medium and small, will be adequate to fit a major proportion of users and that custom manufacturing will be required in a minority of cases only. This should prove to be of large benefit in respect of cost and availability.

It is a further advantage that the upper portion conforms to the shape of the body of the user inasmuch as it will be less prominent and will present a smoother, more natural image.

What is claimed is:

1. A non-ischial weight bearing orthopedic device for use with an orthopedic caliper, comprising:
   a stiff lower portion to which depending components of an orthopedic caliper may be attached in use, said lower portion having an abutment surface positionable to abut the rear of a thigh of a user; and
   an upper portion attached to said lower portion such as to create an extension from said lower portion which provides buttock support in use, said upper portion having an upper extremity adapted to be positioned higher than an ischial tuberosity of the user on the user's buttock, and comprising a moulding having a shape which is concave and generally complementary to the upper rear portion of the user's thigh and the lower portion of the user's buttock when the user is standing, said upper portion being of a stretch resistant material which is deformable so as to conform to the shape of the upper portion of the user's thigh and the user's lower buttock when the user is seated,
   wherein the concave shape and the position of said upper extremity of said upper portion in use causes said upper portion to exert a force having a horizontal component against the buttock and the back of an ischium of the user when the user is standing.

2. An orthopedic device according to claim 1, wherein said upper portion is moulded to said lower portion.

3. In combination, an orthopedic device according to claim 1 and an orthopedic caliper, said device being connected to the upper end of said orthopedic caliper.

4. The combination according to claim 3, said device further comprising attachment means disposed on said lower portion for securing the caliper to the user.

* * * * *